United States Patent
Kalvins et al.

(10) Patent No.: US 8,940,793 B2
(45) Date of Patent: Jan. 27, 2015

(54) 4-[(HALOALKYL)(DIMETHYL)AMMONIO] BUTANOATES AND USE THEREOF IN THE TREATMENT OF CARDIOVASCULAR DISEASE

(75) Inventors: Ivars Kalvins, Ikskile (LV); Edgars Liepins, Riga (LV); Einars Loza, Jurmala (LV); Maija Dambrova, Riga (LV); Ilmars Stonans, Riga (LV); Daina Lola, Riga (LV); Janis Kuka, Jelgava (LV); Osvalds Pugovics, Riga (LV); Viktors Andrianovs, Riga (LV); Marina Makrecka, Riga (LV); Daina Gustina, Riga (LV); Solveiga Grinberga, Salaspils (LV)

(73) Assignee: JSC Grindeks, Riga (LV)

( * ) Notice: Subject to any disclaimer, the term of this patent is extended or adjusted under 35 U.S.C. 154(b) by 0 days.

(21) Appl. No.: 14/112,117

(22) PCT Filed: Apr. 27, 2012

(86) PCT No.: PCT/EP2012/057807
§ 371 (c)(1),
(2), (4) Date: Oct. 16, 2013

(87) PCT Pub. No.: WO2012/146737
PCT Pub. Date: Nov. 1, 2012

(65) Prior Publication Data
US 2014/0107202 A1    Apr. 17, 2014

(30) Foreign Application Priority Data

Apr. 27, 2011 (EP) ..................................... 11163837
Apr. 27, 2011 (EP) ..................................... 11163838
Apr. 27, 2011 (EP) ..................................... 11163842

(51) Int. Cl.
*A01N 37/30* (2006.01)
*A61K 31/205* (2006.01)
*C07C 229/00* (2006.01)
*C07C 229/12* (2006.01)
*C07C 227/18* (2006.01)

(52) U.S. Cl.
CPC ............. *C07C 229/12* (2013.01); *C07C 227/18* (2013.01)
USPC ........................................... 514/556; 562/574

(58) Field of Classification Search
USPC ........................................... 514/556; 562/574
See application file for complete search history.

(56) References Cited

U.S. PATENT DOCUMENTS

| | | |
|---|---|---|
| 4,451,485 A | 5/1984 | Kalvinsh et al. |
| 5,965,615 A | 10/1999 | Kalvinsh et al. |

FOREIGN PATENT DOCUMENTS

WO    WO 97/06794    2/1997

OTHER PUBLICATIONS

International Search Report with Written Opinion for PCT/EP2012/057807 of 9 Aug. 2012.
Simkhovich, et al., Biochemical Pharmacology, vol. 37, No. 2, p. 195-202, Jan. 15, 1988.

*Primary Examiner* — Marcos Sznaidman
(74) *Attorney, Agent, or Firm* — Hueschen and Sage

(57) ABSTRACT

4-[(Haloalkyl)(dimethyl)ammonio]butanoates of formula

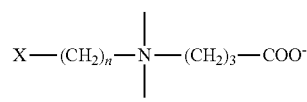

wherein Hal is Cl or F, n=1 or 2,
method for preparing thereof and use thereof for treating cardiovascular disease.

17 Claims, No Drawings

4-[(HALOALKYL)(DIMETHYL)AMMONIO]BUTANOATES AND USE THEREOF IN THE TREATMENT OF CARDIOVASCULAR DISEASE

TECHNICAL FIELD

The present invention relates to new compounds 4-[(haloalkyl)(dimethyl)ammonio]butanoates, and to a method of preparation thereof (compound of formula 6)

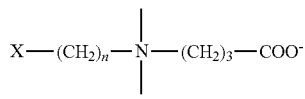

where Hal is Cl or F, n=1 or 2.

The present invention relates also to use of 4-[(haloalkyl)(dimethyl)ammonio]butanoate in the treatment of cardiovascular disease.

BACKGROUND ART

Cardiovascular diseases (CVDs) are a group of disorders of the heart and blood vessels.

An estimated 16.7 million—or 29.2% of total global deaths—result from the various forms of cardiovascular disease (CVD).

Myocardial infarction (heart attack) is a serious result of coronary artery disease. Myocardial infarction (MI) is the irreversible necrosis of heart muscle secondary to prolonged ischemia. A heart attack or myocardial infarction is a medical emergency in which the supply of blood to the heart is suddenly and severely reduced or cut off, causing the muscle to die from lack of oxygen. More than 1.1 million people experience a heart attack (myocardial infarction) each year, and for many of them, the heart attack is their first symptom of coronary artery disease. A heart attack may be severe enough to cause death or it may be silent. As many as one out of every five people have only mild symptoms or none at all, and the heart attack may only be discovered by routine electrocardiography done some time later.

A heart attack (myocardial infarction) is usually caused by a blood clot that blocks an artery of the heart. The artery has often already been narrowed by fatty deposits on its walls. These deposits can tear or break open, reducing the flow of blood and releasing substances that make the platelets of the blood sticky and more likely to form clots. Sometimes a clot forms inside the heart itself, then breaks away and gets stuck in an artery that feeds the heart. A spasm in one of these arteries causes the blood flow to stop.

γ-Butyrobetaine, from which the mammalian organism synthesises carnitine, was primarily characterised as a toxic substance which accelerates respiration, causes salivation and lacrimation, pupil dilation, vasoconstriction and heart stop in diastole LINNEWEH, W. Gamma-Butyrobetain, Crotonbetain und Carnitin im tierischen Stoffwechsel. *Hoppe-Seylers Zeitschfift für physiologische Chemie.* 1929, vol. 181, p. 42-53. At the same time, in later papers other authors ascertained that γ-butyrobetaine is extremely low toxic (LD50>7000 mg/kg, s.c.) ROTZSCH, W. Iber die Toxizitat des Carnitins und einiger verwandter Stoffe. *Acta biol. med. germ.* 1959, vol. 3, p. 28-36.

In the literature data on nonsubstituted γ-butyrobetaine cardiovascular effects are missed, thought it was reported HOSEIN, E. A. Pharmacological actions of γ-butyrobetaine. *Nature.* 1959, vol. 183, p. 328-329. that γ-butyrobetaine is a substance similar to acetyl choline with a prolonged action. However, later the same authors reported that by an error the experiments involved, instead of γ-butyrobetaine, its methyl esther which in fact possesses cholinergic properties. Contrary to the former γ-butyrobetaine was characterised as a pharmacologically inert substance HOSEIN, E. A. Isolation and probable functions of betaine esters in brain metabolism. *Nature.* 1960, vol. 187, p. 321-322.

As structurally related compounds to 4-[(chloromethyl)(dimethyl)ammonio]butanoate are disclosed in:
 GB 1238868 A 14 Jul. 1971 were disclosed betaines, such as 4-trimethylammoniobutanoate, used for polymers. However no pharmacological properties of these betaines weren't presented;
 U.S. Pat. No. 5,973,026 A (XEROX CORP) 26 Oct. 1999 were disclosed 4-trimethylammoniobutanoate and 3-[diethyl(methyl)ammonio]propionate for using for ink compositions;
 LLOYD ANDREW, et al. A comparison of glycine, sarcosine, N,N-dimethylglycine, glycinebetaine and N-modified betaines as liposome cryoprotectants. *Journal of pharmacy and pharmacology.* 1992, vol. 44, no. 6, p. 507-511 disclosed 2-[ethyl(dimethyl)ammonio]acetate used as cryoprotectants for liposomes;
 DAVID B., THOMAS, et al. Synthesis, Characterization, and Aqueous Solution Behavior of Electrolyte- and pH-Responsive Carboxybetaine-Containing Cyclocopolymers. *Macromolecules.* 2003, vol. 36, no. 26, p. 9710-9715 disclose 4-[diallyl(methyl)ammonio]butanoate and its synthesis starting from N,N-diallyl-N-methylaminiom and ethyl 4-bromobutanoate. The free acis is obtained from the ester in a second step using Amberlite ion exchange resin. The product is used as intermediate to synthesise polymers;
 Prelog V. 1930, vol. 2, p. 712-722 disclosed the synthesis of 4-trimethylammoniobutanoate starting from 4-dimethylammoniobutanoate and methyliodide;
 4-Trimethylammoniobutanoate and its synthesis starting from trimethylamine and ethyl 4-bromobutanoate was described JP 2009096766 A (KONAN GAKUEN) 7 May 2009. The free acid is obtained from the ester in a second step using Amberlite ion exchange resin;
 WO 2008/055843 A (KALVINSH IVARS; CHERNOBROVIJS ALEKSANDRS; VARACHEVA LARISA; PUGOVICHS OSVALDS) 15 May 2008 was described 4-trimethylammoniobutanoate and synthesis, which started from the correspondin ester and using KOH-solution;
 CA 2508094 A (VIVIER CANADA INC) 20 Nov. 2006 was disclosed betaines, such as 4-trimethylammoniobutanoate, for use as medicament for accelerating collagen synthesis;
 U.S. Pat. No. 5,965,615 A (TAIHO PHARMACEUTICAL CO LTD; VALSTS ZINATNISKA IESTADE BEZP) 12 Oct. 1999 was disclosed 4-trimethylammoniobutanoate as a medicament for the treatment of myocardial metabolic disorder, the same compound was disclosed in US 2007191381 A (CONCERT PHARMACEUTICALS INC) 16 Aug. 2007 for treatment of myocardial infarction.

3-(2,2,2-Trimethylhydrazinium) propionate dihydrate is known as compound with cardioprotective properties (this substance being known under its International Nonproprietary Name of Meldonium). 3-(2,2,2-Trimethylhydrazinium) propionate is disclosed in U.S. Pat. No. 4,481,218 (INST ORGANICHESKOGO SINTEZA) 6 Nov. 1984 as well in U.S. Pat. No. 4,451,485 A (INSTITU ORCH SINTEZA AKADEMII) 29 May 1984.

It is well known that 3-(2,2,2-trimethylhydrazinium) propionate as dihydrate is widely used for controlling carnitine and gamma-butyrobetaine concentration ratio and consequently the speed of fatty acid beta-oxidation in the body DAMBROVA M., LIEPINSH E., KALVINSH I. I. Mildronate: cardioprotective action through carnitine-lowering effect. *Trends in Cardiovascular Medicine.* 2002, vol. 12, no. 6, p. 275-279.

Due to these properties, Meldonium is extensively applied in medicine as an anti-ischemic, stress-protective and cardioprotective drug in treating various cardiovascular diseases and other pathologies involving tissue ischemia KARPOV R. S., KOSHELSKAYA O. A., VRUBLEVSKY A. V., SOKOLOV A. A., TEPLYAKOV A. T., SKARDA I., DZERVE V., KLINTSARE D., VITOLS A., KALNINS U., KALVINSH I., MATVEYA L., URBANE D. Clinical Efficacy and Safety of Mildronate in Patients With Ischemic Heart Disease and Chronic Heart Failure. *Kardiologiya.* 2000, no. 6, p. 69-74. In the treatment of cardiovascular diseases the mechanism of action of 3-(2,2,2-trimethylhydrazinium)propionate based on limitation of carnitine biosynthesis rate and related long-chain fatty acid transport limitation through mitochondria membranes SIMKHOVICH B. Z., SHUTENKO Z. V., MEIRENA D. V., KHAGI K. B., MEZHAPUKE R. J., MOLODCHINA T. N., KALVINS I. J., LUKEVICS E.

3-(2,2,2,-Trimethylhydrazinium)propionate (THP) a novel gamma-butyrobetaine hydroxylase inhibitor with cardioprotective properties. *Biochemical Pharmacology.* 1988, vol. 37, p. 195-202., KIRIMOTO T., ASAKA N., NAKANO M., TAJIMA K., MIYAKE H., MATSUURA N. Beneficial effects of MET-88, a γ-butyrobetaine hydroxylase inhibitor in rats with heart failure following myocardial infarction. *European Journal of Pharmacology.* 2000, vol. 395, no. 3, p. 217-224.

SUMMARY OF INVENTION

As it was known what Meldonium dihydrate has cardioprotective effect; however there are no data that γ-butyrobetaine itself has pronounced cardioprotective effect. In the patent EP 0845986 B (KALVINSH IVARS, VEVERIS MARIS) 2 Apr. 2003 is disclosed pharmaceutical composition of Meldonium dihydrate and γ-butyrobetaine for use in the treatment of cardiovascular diseases.

An object of the present invention is to provide a compound, which has pronounced cardioprotective effect.

The above-mentioned object is attained by providing new compounds 4-[(haloalkyl)(dimethyl)ammonio]butanoates (compounds of formula 6), that has similar structure to Meldonium or γ-butyrobetaine

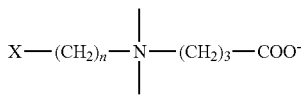

where Hal is Cl or F, n is 1 or 2.

To our surprise 4-[(haloalkyl)(dimethyl)ammonio]butanoates posses pronounced cardioprotective effect and are more effective as Meldonium dihydrate in vivo myocardial infarction models, due this properties 4-[(haloalkyl)(dimethyl)ammonio]butanoates may be used in medicine. 4-[(Haloalkyl)(dimethyl)ammonio]butanoates can be use as a solution of injection and as tablets.

The following object of the present invention is a method of preparation of said compounds of formula 6.

There is disclosed process, which can be used in purpose to prepare target compound 4-[(chloromethyl)(dimethyl)ammonio]butanoate of formula 6 (X=Cl, n=1)), see scheme bellow.

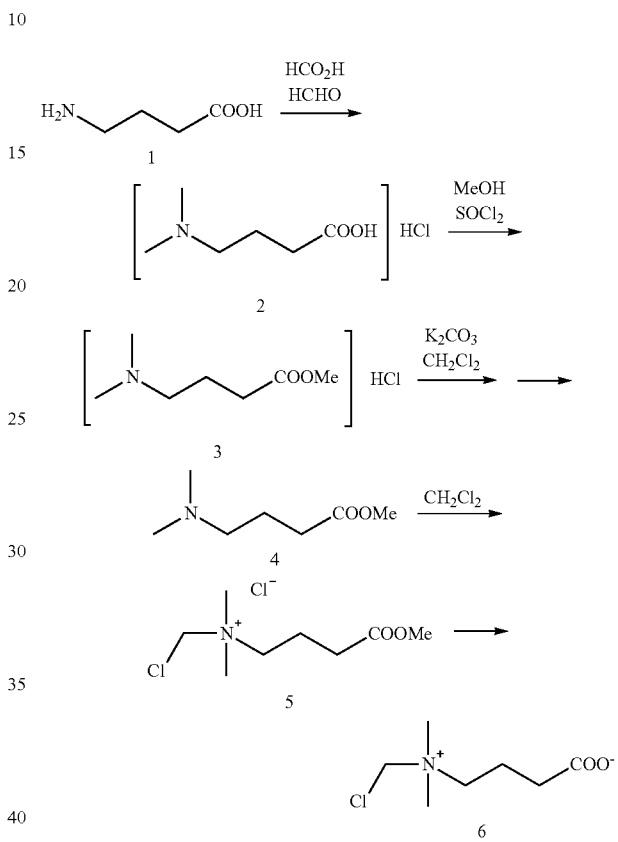

Process for preparing 4-[(chloromethyl)(dimethyl)ammonio]butanoate of formula 6 involves following process steps:

a) adding thionyl chloride to 3-carboxy-N,N-dimethyl-1-propanaminium chloride (2) in appropriate solvent by yielding 4-methoxy-N,N-dimethyl-4-oxo-1-butanaminium chloride (3);

b) suspending 4-methoxy-N,N-dimethyl-4-oxo-1-butanaminium chloride (3) with potassium carbonate in appropriate solvent by obtaining methyl 4-(dimethylamino)butanoate (4);

c) stirring methyl 4-(dimethylamino)butanoate (4) in anhydrous appropriate solvent followed with triturating with diethyl ether by obtaining N-(chloromethyl)-4-methoxy-N,N-dimethyl-4-oxobutan-1-aminium chloride (5);

d) passing N-(chloromethyl)-4-methoxy-N,N-dimethyl-4-oxobutan-1-aminium chloride (5) in appropriate solvent through ion resin column by yielding 4-[(chloromethyl)(dimethyl)ammonio]butanoate (6).

There is also disclosed process, which can be used in purpose to prepare target compound 3-carboxy-N-(2-chloroethyl)-N,N-dimethylpropan-1-aminium chloride of formula 6 (X=Cl, n=2), see scheme bellow.

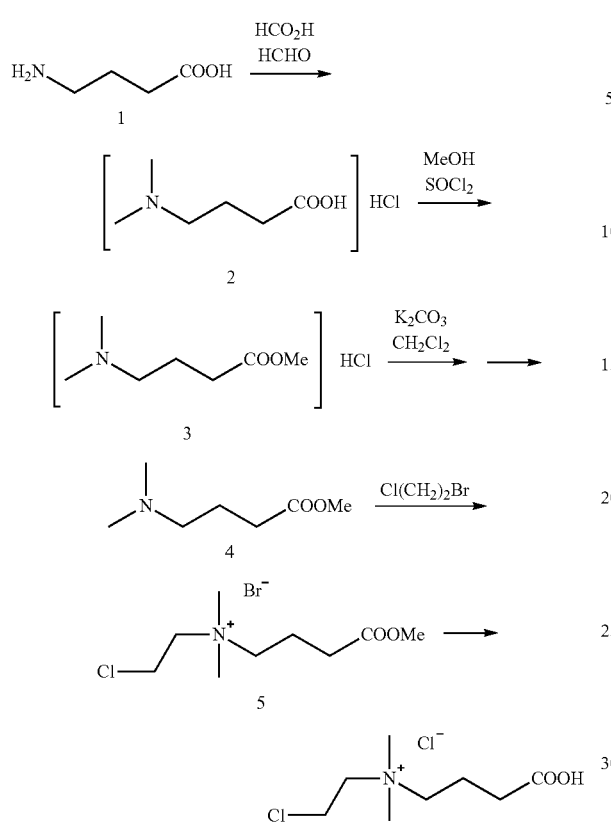

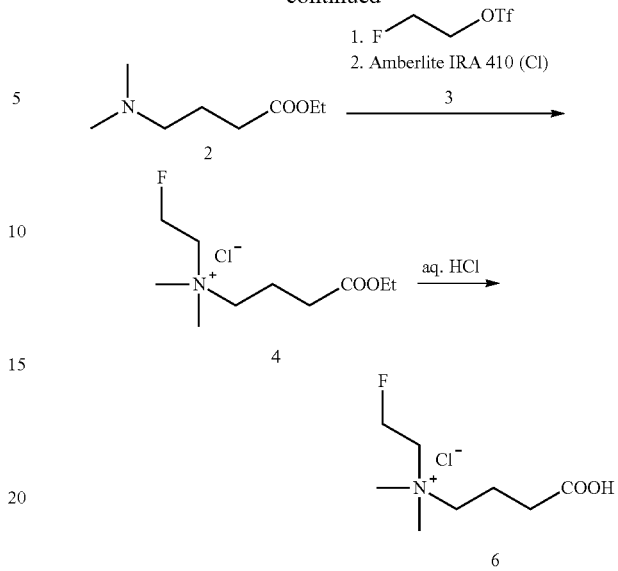

Process for preparing 3-carboxy-N-(2-chloroethyl)-N,N-dimethylpropan-1-aminium chloride of formula 6 (X=Cl, n=2) involves following process steps:

e) adding thionyl chloride to 3-carboxy-N,N-dimethyl-1-propanaminium chloride (2) in appropriate solvent by yielding 4-methoxy-N,N-dimethyl-4-oxo-1-butanaminium chloride (3);

f) suspending 4-methoxy-N,N-dimethyl-4-oxo-1-butanaminium chloride (3) with potassium carbonate in appropriate solvent by obtaining methyl 4-(dimethylamino)butanoate (4);

g) adding 1-bromo-2-chloroethane to methyl 4-(dimethylamino)butanoate (4) in appropriate solvent by obtaining N-(2-chloroethyl)-4-methoxy-N,N-dimethyl-4-oxobutan-1-aminium bromide (5);

passing N-(2-chloroethyl)-4-methoxy-N,N-dimethyl-4-oxobutan-1-aminium bromide (5) in appropriate solvent through ion resin column by yielding 3-carboxy-N-(2-chloroethyl)-N,N-dimethylpropan-1-aminium chloride (6).

There is disclosed process, which can be used in purpose to prepare target compound 3-carboxy-N-(2-fluoroethyl)-N,N-dimethylpropan-1-aminium chloride of formula 6 (X=F, n=2), see scheme bellow.

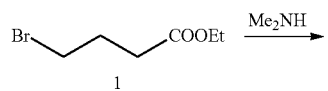

Process for preparing 3-carboxy-N-(2-fluoroethyl)-N,N-dimethylpropan-1-aminium chloride of formula 6 (X=F, n=2) involves following process steps:

h) adding dimethylamine to 4-bromobutanoate (1) in appropriate solvent by yielding ethyl 4-(dimethylamino)butanoate (2);

i) mixing 2-fluoroethyl trifluoromethanesulfonate (3) to 4-(dimethylamino)butanoate (2) in appropriate solvent and passing through ion resin column by yielding 4-ethoxy-N-(2-fluoroethyl)-N,N-dimethyl-4-oxobutan-1-aminium chloride (4);

adding hydrochloride to 4-ethoxy-N-(2-fluoroethyl)-N,N-dimethyl-4-oxobutan-1-aminium chloride (4) in appropriate solvent by obtaining 3-carboxy-N-(2-fluoroethyl)-N,N-dimethylpropan-1-aminium chloride (6).

DESCRIPTION OF EMBODIMENTS

The present invention will be described in more detail by referring to the following nonlimiting examples.

Preparation of
3-carboxy-N,N-dimethyl-1-propanaminium chloride
(2)

3-Carboxy-N,N-dimethyl-1-propanaminium chloride was obtained from 4-aminobutanoic acid (1) in 69-83% yield as described in: T. C. Bruice, S. J. Benkovic. J. Am. Chem. Soc. 1963, 85 (1), 1-8.

Preparation of
4-methoxy-N,N-dimethyl-4-oxo-1-butanaminium
chloride (3)

To a solution of 3-carboxy-N,N-dimethyl-1-propanaminium chloride (2) (45.93 g, 0.27 mol) in anh. methanol (300 ml) at −10-0° C. slowly thionyl chloride (55 ml, 0.76 mol) was added and the temperature of the reaction mixture was allowed to rise to ambient temperature during ca. 1 h. The mixture was stirred at 40-50° C. for 3 h and evaporated. The residue was dissolved in acetone (110 ml) and precipitated by adding ether (400 ml). The solid was filtered, washed with ether, and once more dissolved in acetone (110 ml) followed by the precipitation with ether (400 ml). The precipitate was filtered, washed with ether, and dried to give 38.4 g (77%) of 4-methoxy-N,N-dimethyl-4-oxo-1-butanaminium chloride.

$^1$H NMR (DMSO-$d_6$, HMDSO) δ: 1.91 (qui, J=7.7 Hz, 2H); 2.43 (t, J=7.74 Hz, 2H); 2.71 (d, J=4.9 Hz, 6H); 2.98-3.06 (m, 2H), 3.61 (s, 3H); 10.76 (b s, 1H).

Preparation of methyl 4-(dimethylamino)butanoate (4)

A suspension of 4-methoxy-N,N-dimethyl-4-oxo-1-butanaminium chloride (3) (5.44 g, 0.03 mol) and anh. $K_2CO_3$ (5.52 g, 0.04 mol) in dichloromethane (70 ml) was vigorously stirred at ambient temperature for 24 h. The precipitate was filtered, washed with dichloromethane, and the filtrate was evaporated. The residue was distilled at 32-35° C./3-4 mm Hg to give 2.88 g (66%) of methyl 4-(dimethylamino)butanoate.

$^1$H NMR (DMSO-$d_6$, HMDSO) δ: 1.64 (qui, J=7.2 Hz, 2H); 2.09 (s, 6H); 2.17 (t, J=7.1 Hz, 2H); 2.30 (t, J=7.4 Hz, 2H); 3.57 (s, 3H).

Preparation of N-(chloromethyl)-4-methoxy-N,N-dimethyl-4-oxobutan-1-aminium chloride (5)

A solution of methyl 4-(dimethylamino)butanoate (4) (3.39 g, 23.35 mmol) in anhydrous dichloromethane (50 ml) was stirred for 3 days at ambient temperature and 3 days under reflux. The reaction mixture was evaporated and the oily solid was triturated with diethyl ether (30 ml) in an ultrasound bath. The crystals were filtered, washed with diethyl ether and dried in vacuo over $P_2O_5$ to afford 2.36 g (44%) of N-(chloromethyl)-4-methoxy-N,N-dimethyl-4-oxobutan-1-aminium chloride.

$^1$H NMR ($D_2O$, DSS) δ: 2.12 (m, 2H); 2.56 (t, J=7.0 Hz, 2H); 3.24 (s, 6H); 3.52 (m, 2H); 3.73 (s, 3H); 5.19 (s, 2H).

Preparation of 4-[(chloromethyl)(dimethyl)ammonio]butanoate (6)

A solution of N-(chloromethyl)-4-methoxy-N,N-dimethyl-4-oxobutan-1-aminium chloride (5) (2.39 g, 10.38 mmol) in water (10 ml) was passed through Amberlite® IRA-410 (OH) ion exchange resin column (100 ml) slowly (ca. 0.5 ml/min) eluting with water. To the eluate Dowex® 50WX8 ion exchange resin by small portions was added until the pH of the medium of the initial 9.5 was decreased up to 6.8-7.0 (pH control by a pH-meter). The reaction mixture was filtered, evaporated, and the residue was azeotropically dried successively with acetone, isopropanol, and acetonitrile followed by drying in vacuo over $P_2O_5$ to give 1.69 g (91%) of 4-[(chloromethyl)(dimethyl)ammonio]butanoate. M.p. 100.5-101° C.

$^1$H NMR ($D_2O$, DSS) δ: 2.04 (m, 2H); 2.29 (t, J=7.1 Hz, 2H); 3.23 (s, 6H); 3.48 (m, 2H); 5.17 (s, 2H). LCMS (ESI$^+$, m/z): 180 [M+H]$^+$.

Anal. Calc. for $C_7H_{14}ClNO_2 \cdot 0.98H_2O$ (8.9%): C, 42.61; H, 8.15; N, 7.10.

Found: C, 42.63; H, 8.84; N, 6.98.

Preparation of 3-carboxy-N,N-dimethyl-1-propanaminium chloride (2)

3-Carboxy-N,N-dimethyl-1-propanaminium chloride was obtained from 4-aminobutanoic acid (1) in 69-83% yield as described in: T. C. Bruice, S. J. Benkovic. J. Am. Chem. Soc. 1963, 85 (1), 1-8.

Preparation of 4-methoxy-N,N-dimethyl-4-oxo-1-butanaminium chloride (3)

To a solution of 3-carboxy-N,N-dimethyl-1-propanaminium chloride (2) (45.93 g, 0.27 mol) in anh. methanol (300 ml) at −10-0° C. slowly thionyl chloride (55 ml, 0.76 mol) was added and the temperature of the reaction mixture was allowed to rise to ambient temperature during ca. 1 h. The mixture was stirred at 40-50° C. for 3 h and evaporated. The residue was dissolved in acetone (110 ml) and precipitated by adding ether (400 ml). The solid was filtered, washed with ether, and once more dissolved in acetone (110 ml) followed by the precipitation with ether (400 ml). The precipitate was filtered, washed with ether, and dried to give 38.4 g (77%) of 4-methoxy-N,N-dimethyl-4-oxo-1-butanaminium chloride.

$^1$H NMR (DMSO-$d_6$, HMDSO) δ: 1.91 (qui, J=7.7 Hz, 2H); 2.43 (t, J=7.74 Hz, 2H); 2.71 (d, J=4.9 Hz, 6H); 2.98-3.06 (m, 2H), 3.61 (s, 3H); 10.76 (b s, 1H).

Preparation of methyl 4-(dimethylamino)butanoate (4)

A suspension of 4-methoxy-N,N-dimethyl-4-oxo-1-butanaminium chloride (3) (5.44 g, 0.03 mol) and anh. $K_2CO_3$ (5.52 g, 0.04 mol) in dichloromethane (70 ml) was vigorously stirred at ambient temperature for 24 h. The precipitate was filtered, washed with dichloromethane, and the filtrate was evaporated. The residue was distilled at 32-35° C./3-4 mm Hg to give 2.88 g (66%) of methyl 4-(dimethylamino)butanoate.

$^1$H NMR (DMSO-$d_6$, HMDSO) δ: 1.64 (qui, J=7.2 Hz, 2H); 2.09 (s, 6H); 2.17 (t, J=7.1 Hz, 2H); 2.30 (t, J=7.4 Hz, 2H); 3.57 (s, 3H).

Preparation of N-(2-chloroethyl)-4-methoxy-N,N-dimethyl-4-oxobutan-1-aminium bromide (5)

To a solution of methyl 4-(dimethylamino)butanoate (4) (4.00 g, 27.6 mmol) in acetonitrile (50 ml) 1-bromo-2-chloroethane (23 ml, 276 mmol) was added and the obtained mixture was stirred in a closed vessel at 65° C. for 5 days. The reaction mixture was evaporated; the white solid residue was washed with diethyl ether and dried in vacuo over $P_2O_5$ to give 7.477 g (94%) of N-(2-chloroethyl)-4-methoxy-N,N-dimethyl-4-oxobutan-1-aminium bromide.

$^1$H NMR ($D_2O$, DSS) δ: 2.13 (m, 2H); 2.54 (t, J=7.0 Hz, 2H); 3.20 (s, 6H); 3.45 (m, 2H); 3.73 (s, 3H); 3.80 (t, J=6.7 Hz, 2H); 4.03 (t, J=6.7 Hz, 2H). LCMS (ESI$^+$, m/z): 208 [M-Br$^-$]$^+$ (for $^{35}$Cl).

Preparation of 3-carboxy-N-(2-chloroethyl)-N,N-dimethylpropan-1-aminium chloride (6)

N-(2-Chloroethyl)-4-methoxy-N,N-dimethyl-4-oxobutan-1-aminium bromide (5) (7.477 g, 25.9 mmol) was dissolved in water (10 ml) and passed through Amberlite® IRA-410 (Cl) ion exchange resin column (100 ml) slowly (ca. 0.5 ml/min) eluting with water (control with 2% $AgNO_3$ solution). The eluate was evaporated; the residue (~6 g) was dissolved in 1N HCl (50 ml) and stirred for 15 h at 70° C. The reaction mixture was evaporated and dried to give 4.755 g (79%) of 3-carboxy-N-(2-chloroethyl)-N,N-dimethylpropan-1-aminium chloride as a yellowish solid. The purity of the obtained compound can be increased by crystallization from acetonitrile. Thus, 2 g of the obtained material was crystallized from acetonitrile (120 ml) to afford 1.32 g of white crystalline 6 with m.p. 130° C.

¹H NMR (D₂O, DSS) δ: 2.11 (m, 2H); 2.52 (t, J=7.0 Hz, 2H); 3.20 (s, 6H); 3.46 (m, 2H); 3.80 (t, J=6.7 Hz, 2H); 4.03 (t, J=6.7 Hz, 2H). LCMS (ESI⁺, m/z): 194 [M-Cl⁻]⁺ (for ³⁵Cl).

Anal. Calc. for $C_8H_{17}Cl_2NO_2 \cdot 0.49H_2O$ (3.7%): C, 40.21; H, 7.58; N, 5.86.

Found: C, 40.20; H, 7.63; N, 5.66.

Preparation of ethyl 4-(dimethylamino)butanoate (2)

To a solution of ethyl 4-bromobutanoate (1) (20.0 g, 102.5 mmol) in anhydrous ethanol (200 ml) a 33% (~5.6 M) solution of dimethylamine in ethanol (100 ml, 560 mmol) was added and the resulting mixture was stirred at ambient temperature for 24 h. The reaction mixture was evaporated, the residue was dissolved in chloroform (200 ml), washed successively with saturated solutions of NaHCO₃ (4×50 ml) and NaCl (50 ml), and dried (Na₂SO₄). The solution was evaporated and the residue (12.15 g) was distilled in vacuo at 69-72° C./13 mm Hg to give 10.66 g (65%) of the ethyl 4-(dimethylamino)butanoate.

¹H NMR (DMSO-d₆, HMDSO) δ: 1.25 (t, J=7.2 Hz, 3H); 1.78 (qui, J=7.4 Hz, 2H); 2.21 (s, 6H); 2.27 (t, J=7.3 Hz, 2H); 2.32 (t, J=7.5 Hz, 2H); 4.12 (q, J=7.2 Hz, 2H).

Preparation of 2-fluoroethyl trifluoromethanesulfonate (3)

2-Fluoroethyl trifluoromethanesulfonate (3) was obtained as described in: C. L. Falzon, U. Ackermann, N. Spratt, H. J. Tochon-Danguy, J. White, D. Howells, A. M. Scott. *J. Label. Compd. Radiopharm.* 2006, 49, 1089-1103: To a suspension of poly(4-vinylpyridine) (6.68 g, 60.78 mmol) in anhydrous dichloromethane (100 ml) under argon atmosphere trifluoromethanesulphonic anhydride (8.57 g, 30.37 mmol) was added and the reaction mixture was stirred at ambient temperature for 15 min. To the mixture 2-fluoroethanol (1.346 g, 21.30 mmol) was added, the resulting mixture was stirred for 30 min. at ambient temperature and filtered under gravity. The precipitate was washed with dichloromethane (30 ml), the filtrates were combined, washed successively with saturated solutions of NaHCO₃ (4×50 ml) and NaCl (2×50 ml), and dried (Na₂SO₄). The solvent was evaporated at 20° C./200 mm Hg and the obtained crude 2-Fluoroethyl trifluoromethanesulfonate (3) was used in the next step without further purification.

¹H NMR (CDCl₃, HMDSO δ): 4.65 (m, 2H, $^2J_{F,H}$~47 Hz), 4.66 (m, 2H, $^3J_{F,H}$~27 Hz).

Preparation of 4-ethoxy-N-(2-fluoroethyl)-N,N-dimethyl-4-oxobutan-1-aminium chloride (4)

To a solution of ethyl 4-(dimethylamino)butanoate (2) (2.26 g, 14.2 mmol) in anhydrous dichloromethane (20 ml) at ice bath temperature the crude 2-fluoroethyl trifluoromethanesulfonate (3), obtained in the preceding step from 1.346 g (21.30 mmol) of 2-fluoroethanol, was added. The reaction mixture was stirred at ice bath temperature for 1 h and evaporated. The dark oily residue (5.431 g) was dissolved in water (15 ml), filtered through a pad of cotton and passed through Amberlite® IRA-410 (Cl) ion exchange resin column (50 ml) slowly (ca. 0.5 ml/min) eluting with water (control with 2% AgNO₃ solution). The eluate was evaporated and the residue was azeotropically dried successively with acetone, isopropanol, and acetonitrile to give 3.61 g (quant.) of the 4-ethoxy-N-(2-fluoroethyl)-N,N-dimethyl-4-oxobutan-1-aminium chloride (4).

¹H NMR (D₂O, DSS) δ: 1.17 (t, J=7.2 Hz, 3H); 2.12 (m, 2H); 2.52 (t, J=7.0 Hz, 2H); 3.20 (s, 6H); 3.46 (m, 2H); 3.80 (m, $^3J_{F,H}$=28.2 Hz, 2H); 4.19 (q, J=7.2 Hz, 2H); 4.97 (m, $^2J_{F,H}$=47.3 Hz, 2H).

Preparation of 3-carboxy-N-(2-fluoroethyl)-N,N-dimethylpropan-1-aminium chloride (6)

To a solution of 4-ethoxy-N-(2-fluoroethyl)-N,N-dimethyl-4-oxobutan-1-aminium chloride (4) from the preceding step (3.61 g, ≤514.2 mmol) in dioxane (10 ml) was added conc. HCl (5 ml) and the reaction mixture was stirred at 40° C. for 24 h. The mixture was evaporated, to the residue (3.02 g) was added conc.HCl (15 ml) and stirred at 70° C. for 2 h, then the mixture was evaporated again. The residue was triturated with acetonitrile in an ultrasound bath, then the mixture was decanted and the crystalline solid was washed with acetone. After drying in vacuo over P₂O₅ 2.125 g of the 3-carboxy-N-(2-fluoroethyl)-N,N-dimethylpropan-1-aminium chloride (6) was obtained.

¹H NMR (D₂O, DSS) δ: 2.11 (m, 2H); 2.52 (t, J=7.0 Hz, 2H); 3.20 (s, 6H); 3.47 (m, 2H); 3.80 (m, $^3J_{F,H}$=28.3 Hz, 2H); 4.98 (m, $^2J_{F,H}$=47.3 Hz, 2H). LCMS (ESI⁺, m/z): 178 [M-Cl⁻]⁺.

Anal. Calcd for $C_8H_{17}ClFNO_2 \cdot 0.3H_2O$ (2.5%): C, 43.86; H, 8.10; N, 6.39. Found: C, 43.86; H, 8.10; N, 6.39.

Cardioprotective Activity

Fifty male, 10 weeks old Wistar rats weighing 200-250 g were housed under standard conditions (21-23° C., 12 h light-dark cycle) with unlimited access to food (R3 diet, Lactamin AB, Sweden) and water.

Rats were adapted to local conditions for two weeks before the start of treatment. Meldonium dihydrate at a dose of 20 mg/kg, gamma-butyrobetaine at a dose of 20 mg/kg and 4-[(chloromethyl)(dimethyl) ammonio]butanoate at dose of 20 mg/kg were administered p.o. daily for 8 weeks. Control rats received water.

Isolated Rat Heart Infarction Study

The isolated rat heart experiment was performed essentially as described earlier (Liepinsh et al., *J. Cardiovasc. Pharmacol.* 2006; 48(6):314-9). Twenty-four hours after the last drug administration hearts were excised and retrogradely perfused via the aorta at a constant pressure with oxygenated Krebs-Henseleit buffer at 37° C. The heart rate, left ventricle end-diastolic pressure and left ventricle developed pressure were continuously recorded. Coronary flow was measured using an ultrasound flow detector (HSE) and the PowerLab 8/30 system from ADInstruments. The hearts were perfused for 20 min to stabilize the hemodynamic functions and then occlusion was performed for 60 min by constricting threads through a plastic tube. Successful occlusion was confirmed by a coronary flow decrease of about 40 percent. Reperfusion was achieved by releasing the threads. At the end of the 150-min reperfusion period, the risk zone was delineated with 0.1% methylene blue. The hearts were then sectioned transversely from the apex to the base in five slices 2 mm in thickness and incubated in 1% triphenyltetrazolium chloride in phosphate buffer (pH 7.4, 37° C.) for 10 min to stain viable tissue red and necrotic tissue white. Computerized planemetric analysis of Sony A900 photographs was performed using Image-Pro Plus 6.3 software to determine the area at risk and area of necrosis expressed as a % of the left ventricle. The obtained values were then used to calculate the infarct size (IS) as a % of risk area according to the formula:

Infarct Size=Area of Necrosis/Area at Risk×100%.

Effects in Isolated Rat Heart Infarction Model

The anti-infarction effect of examined substances was investigated in an isolated rat heart infarction model. During occlusion of left coronary artery, the coronary flow in all experimental groups was decreased for 40% (from 11 ml/min to 7 ml/min). Moreover, the drop of developed left ventricular pressure for 50% was observed. The heart rate during the occlusion period did not change significantly. In reperfusion stage, coronary flow, developed left ventricular pressure, ±dp/dt values were recovered till about 80% of control level. There were no significant differences between control and treatment groups.

Effects of Meldonium dihydrate (20 mg/kg), gamma-butyrobetaine (20 mg/kg) and 4-[(chloromethyl)(dimethyl)ammonio]butanoate (20 mg/kg) after 2 weeks of treatment on infarct size in the isolated rat heart infarction experiment are presented in Table 1.

TABLE 1

Effects of Meldonium dihydrate, gamma-butyrobetaine and 4-[(chloromethyl) (dimethyl)ammonio]butanoate on infarct size

|  | Infarct size, % of control |
|---|---|
| Control | 100.0 ± 5.9 |
| Meldonium dihydrate 20 mg/kg | 117.9 ± 7.9 |
| Gamma-butyrobetaine 20 mg/kg | 87.6 ± 11.4 |
| 4-[(Chloromethyl)(dimethyl)ammonio]butanoate 20 mg/kg | 65.2 ± 6.8*,#,$ |

Each value represents the mean ± s.e.m. of 9-10 animals.
*p < 0.05 compared with control group;
p < 0.05 compared with Gamma-butyrobetaine group,
$p < 0.05 compared with Meldonium dihydrate group As it is presented in Table 1, Meldonium dihydrate treatment at a dose of 20 mg/kg had no therapeutical effect; gamma-butyrobetaine was decreased infarct size nearly by 12.4%. 4-[(Chloromethyl)(dimethyl)ammonio]butanoate at dose of 20 mg/kg observed the best therapeutical effect decreasing infarct size by 34.8%.

Cardioprotective Activity

Fifty male, 10 weeks old Wistar rats weighing 200-250 g were housed under standard conditions (21-23° C., 12 h light-dark cycle) with unlimited access to food (R3 diet, Lactamin AB, Sweden) and water.

Rats were adapted to local conditions for two weeks before the start of treatment. Meldonium dihydrate at a dose of 20 mg/kg, gamma-butyrobetaine at a dose of 20 mg/kg and 3-carboxy-N-(2-chloroethyl)-N,N-dimethylpropan-1-aminium chloride at dose of 20 mg/kg were administered p.o. daily for 8 weeks. Control rats received water.

Isolated Rat Heart Infarction Study

The isolated rat heart experiment was performed essentially as described earlier (Liepinsh et al., J. Cardiovasc. Pharmacol. 2006; 48(6):314-9). Twenty-four hours after the last drug administration hearts were excised and retrogradely perfused via the aorta at a constant pressure with oxygenated Krebs-Henseleit buffer at 37° C. The heart rate, left ventricle end-diastolic pressure and left ventricle developed pressure were continuously recorded. Coronary flow was measured using an ultrasound flow detector (HSE) and the PowerLab 8/30 system from ADInstruments. The hearts were perfused for 20 min to stabilize the hemodynamic functions and then occlusion was performed for 60 min by constricting threads through a plastic tube. Successful occlusion was confirmed by a coronary flow decrease of about 40 percent. Reperfusion was achieved by releasing the threads. At the end of the 150-min reperfusion period, the risk zone was delineated with 0.1% methylene blue. The hearts were then sectioned transversely from the apex to the base in five slices 2 mm in thickness and incubated in 1% triphenyltetrazolium chloride in phosphate buffer (pH 7.4, 37° C.) for 10 min to stain viable tissue red and necrotic tissue white. Computerized planemetric analysis of Sony A900 photographs was performed using Image-Pro Plus 6.3 software to determine the area at risk and area of necrosis expressed as a % of the left ventricle. The obtained values were then used to calculate the infarct size (IS) as a % of risk area according to the formula:

Infarct Size=Area of Necrosis/Area at Risk×100%.

Effects in Isolated Rat Heart Infarction Model

The anti-infarction effect of examined substances was investigated in an isolated rat heart infarction model. During occlusion of left coronary artery, the coronary flow in all experimental groups was decreased for 40% (from 11 ml/min to 7 ml/min). Moreover, the drop of developed left ventricular pressure for 50% was observed. The heart rate during the occlusion period did not change significantly. In reperfusion stage, coronary flow, developed left ventricular pressure, ±dp/dt values were recovered till about 80% of control level. There were no significant differences between control and treatment groups.

Effects of Meldonium dihydrate (20 mg/kg), gamma-butyrobetaine (20 mg/kg) and 3-carboxy-N-(2-chloroethyl)-N,N-dimethylpropan-1-aminium chloride (20 mg/kg) after 2 weeks of treatment on infarct size in the isolated rat heart infarction experiment are presented in Table 2.

TABLE 2

Effects of Meldonium dihydrate, gamma-butyrobetaine and 3-carboxy-N-(2-chloroethyl)-N,N-dimethylpropan-1-aminium chloride on infarct size

|  | Infarct size, % of control |
|---|---|
| Control | 100.0 ± 5.9 |
| Meldonium dihydrate 20 mg/kg | 117.9 ± 7.9 |
| Gamma-butyrobetaine 20 mg/kg | 87.6 ± 11.4 |
| 3-Carboxy-N-(2-chloroethyl)-N,N-dimethylpropan-1-aminium chloride 20 mg/kg | 59.9 ± 7.6*,#,$ |

Each value represents the mean ± s.e.m. of 9-10 animals.
*p < 0.05 compared with control group;
p < 0.05 compared with Gamma-butyrobetaine group,
$p < 0.05 compared with Meldonium dihydrate group As it is presented in Table 2, Meldonium dihydrate treatment at a dose of 20 mg/kg had no therapeutical effect; gamma-butyrobetaine was decreased infarct size nearly by 12.4%. 3-Carboxy-N-(2-chloroethyl)-N,N-dimethylpropan-1-aminium chloride at dose of 20 mg/kg observed the best therapeutical effect decreasing infarct size by 41.1%.

The same experimental conditions as above were used for testing 3-carboxy-N-(2-fluoroethyl)-N,N-dimethylpropan-1-aminium chloride.

Effects of Meldonium dihydrate (20 mg/kg), gamma-butyrobetaine (20 mg/kg) and 3-carboxy-N-(2-fluoroethyl)-N,N-dimethylpropan-1-aminium chloride (20 mg/kg) after 2 weeks of treatment on infarct size in the isolated rat heart infarction experiment are presented in Table 3.

TABLE 3

Effects of Meldonium dihydrate, gamma-butyrobetaine and 3-carboxy-N-(2-fluoroethyl)-N,N-dimethylpropan-1-aminium chloride on infarct size

| | Infarct size, % of control |
|---|---|
| Control | 100.0 ± 5.9 |
| Meldonium dihydrate 20 mg/kg | 117.9 ± 7.9 |
| Gamma-butyrobetaine 20 mg/kg | 87.6 ± 11.4 |
| 3-carboxy-N-(2-fluoroethyl)-N,N-dimethylpropan-1-aminium chloride 20 mg/kg | 65.5 ± 9.1*,#,$ |

Each value represents the mean ± s.e.m. of 9-10 animals.
*$p < 0.05$ compared with control group;
$p < 0.05$ compared with Gamma-butyrobetaine group,
$$p < 0.05$ compared with Meldonium dihydrate group As it is presented in Table 3, Meldonium dihydrate treatment at a dose of 20 mg/kg had no therapeutical effect; gamma-butyrobetaine was decreased infarct size nearly by 12.4%. 3-Carboxy-N-(2-fluoroethyl)-N,N-dimethylpropan-1-aminium chloride at dose of 20 mg/kg observed the best therapeutical effect decreasing infarct size by 34.5%.

The invention claimed is:

1. A 4-[(haloalkyl)(dimethyl)ammonio]butanoate of formula

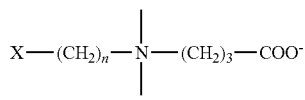

wherein X is Cl or F and n is 1 or 2, or a pharmaceutically acceptable salt thereof.

2. The 4-[(haloalkyl)(dimethyl)ammonio]butanoate of claim 1 which is selected from the group consisting of:
    4-[(chloromethyl)(dimethyl)ammonio]butanoate,
    3-Carboxy-N-(2-chloroethyl)-N,N-dimethylpropan-1-aminium chloride, and
    3-Carboxy-N-(2-fluoroethyl)-N,N-dimethylpropan-1-aminium chloride.

3. A process for preparing the 4-[(haloalkyl)(dimethyl)ammonio]butanoate of claim 1 which is 4-[(chloromethyl)(dimethyl)ammonio]butanoate, comprising:
    a. adding thionyl chloride to 3-carboxy-N,N-dimethyl-1-propanaminium chloride in appropriate solvent to yield 4-methoxy-N,N-dimethyl-4-oxo-1-butanaminium chloride;
    b. suspending 4-methoxy-N,N-dimethyl-4-oxo-1-butanaminium chloride with potassium carbonate in appropriate solvent to obtain methyl 4-(dimethylamino)butanoate;
    c. stirring methyl 4-(dimethylamino)butanoate in an appropriate anhydrous solvent followed with triturating with diethyl ether to obtain N-(chloromethyl)-4-methoxy-N,N-dimethyl-4-oxobutan-1-aminium chloride; and
    d. passing N-(chloromethyl)-4-methoxy-N,N-dimethyl-4-oxobutan-1-aminium chloride in appropriate solvent through ion resin column to yield 4-[(chloromethyl)(dimethyl)ammonio]butanoate.

4. The process according to claim 3, wherein in step a) the appropriate solvent is methanol.

5. The process according to claim 3, wherein in step b) the appropriate solvent is dichloromethane.

6. The process according to claim 3, wherein in step c) the appropriate anhydrous solvent is dichloromethane.

7. The process according to claim 3, wherein in step d) the appropriate solvent is water.

8. A process for preparing the 4-[(haloalkyl)(dimethyl)ammonio]butanoate according to claim 1, which is 3-carboxy-N-(2-chloroethyl)-N,N-dimethylpropan-1-aminium chloride, comprising:
    e. adding thionyl chloride to 3-carboxy-N,N-dimethyl-1-propanaminium chloride in appropriate solvent to yield 4-methoxy-N,N-dimethyl-4-oxo-1-butanaminium chloride;
    f. suspending 4-methoxy-N,N-dimethyl-4-oxo-1-butanaminium chloride with potassium carbonate in an appropriate solvent to obtain methyl 4-(dimethylamino)butanoate;
    g. adding 1-bromo-2-chloroethane to methyl 4-(dimethylamino)butanoate in appropriate solvent to obtain NV-(2-chloroethyl)-4-methoxy-N,N-dimethyl-4-oxobutan-1-aminium bromide; and
    h. passing N-(2-chloroethyl)-4-methoxy-N,N-dimethyl-4-oxobutan-1-aminium bromide in appropriate solvent through ion resin column to yield 3-carboxy-N-(2-chloroethyl)-N,N-dimethylpropan-1-aminium chloride.

9. The process according to claim 8, wherein in step e) the appropriate solvent is methanol.

10. The process according to claim 8, wherein in step f) the appropriate solvent is dichloromethane.

11. The process according to claim 8, wherein in step g) the appropriate solvent is acetonitrile.

12. The process according to claim 8, wherein in a step h) the appropriate solvent is water.

13. A process for preparing the 4-[(haloalkyl)(dimethyl)ammonio]butanoate of claim 1 which is 3-carboxy-N-(2-fluoroethyl)-N,N-dimethylpropan-1-aminium chloride, comprising:
    i. adding dimethylamine to 4-bromobutanoate in appropriate solvent to yield ethyl 4-(dimethylamino)butanoate;
    j. mixing 2-fluoroethyl trifluoromethanesulfonate to 4-(dimethylamino)butanoate in an appropriate solvent and passing through ion resin column to yield 4-ethoxy-N-(2-fluoroethyl)-N,N-dimethyl-4-oxobutan-1-aminium chloride; and
    k. adding hydrochloride to 4-ethoxy-N-(2-fluoroethyl)-N,N-dimethyl-4-oxobutan-1-aminium chloride in an appropriate solvent to obtain 3-carboxy-N-(2-fluoroethyl)-N,N-dimethylpropan-1-aminium chloride.

14. The process according to claim 13, wherein in step i) the appropriate solvent is ethanol.

15. The process according to claim 13, wherein in step j) the appropriate solvent is dichloromethane.

16. The process according to claim 13, wherein in step k) the appropriate solvent is dioxane.

17. A method for treating myocardial infarction in a subject in need thereof, comprising administration of an effective amount of the 4-[(haloalkyl)(dimethyl)ammonio]butanoate according to claim 1.

* * * * *